US010101295B2

(12) United States Patent
Chang et al.

(10) Patent No.: US 10,101,295 B2
(45) Date of Patent: Oct. 16, 2018

(54) ON-CHIP REFERENCE ELECTRODE FOR BIOLOGICALLY SENSITIVE FIELD EFFECT TRANSISTOR

(71) Applicant: Taiwan Semiconductor Manufacturing Co., Ltd., Hsin-Chu (TW)

(72) Inventors: Yi-Hsien Chang, Shetou Township (TW); Chun-Ren Cheng, Hsin-Chu (TW); Shih-Fen Huang, Jhubei (TW); Ching-Hui Lin, Taichung (TW)

(73) Assignee: Taiwan Semiconductor Manufacturing Co., Ltd., Hsin-Chu (TW)

( * ) Notice: Subject to any disclaimer, the term of this patent is extended or adjusted under 35 U.S.C. 154(b) by 29 days.

(21) Appl. No.: 15/386,545

(22) Filed: Dec. 21, 2016

(65) Prior Publication Data

US 2018/0172627 A1    Jun. 21, 2018

Related U.S. Application Data

(60) Provisional application No. 62/434,623, filed on Dec. 15, 2016.

(51) Int. Cl.
| | | |
|---|---|---|
| G01N 27/403 | (2006.01) | |
| G01N 27/414 | (2006.01) | |
| H01L 23/482 | (2006.01) | |
| H01L 29/786 | (2006.01) | |

(52) U.S. Cl.
CPC ..... *G01N 27/4145* (2013.01); *G01N 27/4146* (2013.01); *H01L 23/4825* (2013.01); *H01L 29/786* (2013.01)

(58) Field of Classification Search
CPC ................ G01N 27/4145; G01N 27/4146
USPC ......................................... 257/253
See application file for complete search history.

(56) References Cited

U.S. PATENT DOCUMENTS

| | | |
|---|---|---|
| 5,369,246 A | 11/1994 | Nanos |
| 7,666,285 B1 * | 2/2010 | Cho ............... B01L 3/502715 137/814 |
| 7,728,401 B2 | 6/2010 | Takatori |
| 8,405,169 B2 | 3/2013 | Cheng et al. |
| 8,569,808 B1 | 10/2013 | Chen et al. |

(Continued)

OTHER PUBLICATIONS

U.S. Appl. No. 15/216,853, filed Jul. 22, 2016.

(Continued)

*Primary Examiner* — Igwe U Anya
(74) *Attorney, Agent, or Firm* — Eschweiler & Potashnik, LLC (57) ABSTRACT

A semiconductor device including a biosensor with an on-chip reference electrode embedded within the semiconductor device, and associated manufacturing methods are provided. In some embodiments, a pair of source/drain regions is disposed within a device substrate and separated by a channel region. An isolation layer is disposed over the device substrate. A sensing well is disposed from an upper surface of the isolation layer overlying the channel region. A bio-sensing film is disposed along the upper surface of the isolation layer and extended along sidewall and lower surfaces of the sensing well. A reference electrode is disposed vertically between the bio-sensing film and the isolation layer.

20 Claims, 8 Drawing Sheets

(56) References Cited

U.S. PATENT DOCUMENTS

| | | | |
|---|---|---|---|
| 8,728,844 | B1 | 5/2014 | Liu et al. |
| 8,762,925 | B2 | 6/2014 | Chen et al. |
| 8,791,557 | B2 | 7/2014 | Chang et al. |
| 8,846,416 | B1 | 9/2014 | Chu et al. |
| 8,901,003 | B1 | 12/2014 | Pan |
| 9,528,939 | B2 | 12/2016 | Duer |
| 2002/0017916 | A1 | 2/2002 | Costello |
| 2005/0123680 | A1* | 6/2005 | Kang ............... A61B 5/14532 427/248.1 |
| 2006/0057771 | A1 | 3/2006 | Kovacs |
| 2006/0197118 | A1 | 9/2006 | Migliorato et al. |
| 2007/0210350 | A1 | 9/2007 | Omura |
| 2007/0210807 | A1* | 9/2007 | Arisaka ............... G01N 27/225 324/664 |
| 2008/0063566 | A1* | 3/2008 | Matsumoto ........ G01N 33/5438 422/68.1 |
| 2009/0065761 | A1 | 3/2009 | Chen |
| 2010/0230578 | A1 | 9/2010 | Horikoshi et al. |
| 2010/0248284 | A1* | 9/2010 | Chen ............... G01N 33/48728 435/29 |
| 2011/0209555 | A1 | 9/2011 | Ahles |
| 2011/0291673 | A1* | 12/2011 | Shibata ............. G01N 27/4145 324/649 |
| 2012/0021918 | A1 | 1/2012 | Bashir et al. |
| 2012/0032235 | A1 | 2/2012 | Bikumandla |
| 2013/0105868 | A1* | 5/2013 | Kalnitsky ........... G01N 27/414 257/288 |
| 2013/0200438 | A1 | 8/2013 | Liu et al. |
| 2013/0256259 | A1 | 10/2013 | Chang et al. |
| 2013/0293878 | A1 | 11/2013 | Chang et al. |
| 2013/0307626 | A1 | 11/2013 | Mohammadi |
| 2013/0341734 | A1 | 12/2013 | Merz |
| 2014/0073039 | A1 | 3/2014 | Chang et al. |
| 2014/0134748 | A1 | 5/2014 | Liu et al. |
| 2014/0225166 | A1 | 8/2014 | Ellis-Monaghan et al. |
| 2014/0256030 | A1 | 9/2014 | Shen et al. |
| 2014/0264467 | A1 | 9/2014 | Cheng et al. |
| 2014/0264468 | A1 | 9/2014 | Cheng et al. |
| 2014/0308752 | A1 | 10/2014 | Chang |
| 2014/0335640 | A1 | 11/2014 | Chang et al. |
| 2014/0370636 | A1 | 12/2014 | Dalton et al. |
| 2015/0129937 | A1 | 5/2015 | Chen et al. |
| 2015/0330941 | A1* | 11/2015 | Smith .................. H01L 29/786 257/253 |
| 2016/0209355 | A1 | 7/2016 | Chang et al. |
| 2017/0018626 | A1 | 1/2017 | Hoffman |

OTHER PUBLICATIONS

Non Final Office Action dated Feb. 14, 2017 U.S. Appl. No. 15/216,853.

Final Office Action dated Jul. 27, 2017 in connection with U.S. Appl. No. 14/719,991.

Notice of Allowance dated Mar. 15, 2017 in connection with U.S. Appl. No. 14/600,315.

Jang, et al. "Performance Enhancement of Capacitive-Coupling Dual-Gate Ion-Sensitive Field-Effect Transistor in Ultra-Thin-Body." Scientific Reports, 4: 5284. Published Jun. 13, 2014.

Romero-Garcia, et al.; "Silicon Nitride CMOS-compatible Platform for Integrated Photonics Applications at Visible Wavelengths;" Optics Express, vol. 21, No. 12, Jun. 17, 2013, p. 1-11.

Salm, et al. "Ultralocalized Thermal Reactions in Subnanoliter Droplets-in-air;" PNAS; vol. 110; No. 9; Feb. 26, 2013; p. 3310-3315.

"Supporting Information for Ultralocalized Thermal Reactions in Subnanoliter Droplets-in-air;" PNAS, vol. 110; No. 9, Febraury 26, 2013, p. 1-25.

Lee, et al.; "Microchip-based one step DNA Extraction and Real-Time PCR in one Chamber for Rapid Pathogen Identification;" Lab Chip; The Royal Society of Chemistry 2006; p. 886-895.

Dametto, Paolo; "DNA Amplification and Detection Using a pH-Sensing System: Implications for Current Analytical Technologies and Point-of-Care Nucleic Acid Tests;" Aug. 2013; p. 1-31.

Bhattacharya, et al.; "PCR-Based Detection in a Micro-Fabricated Platform;" Lab Chip; The Royal Society of Chemistry; 2008; p. 1130-1136.

Toumazou, et al. "Simultaneous DNA amplification and detection using a pH-sensing semiconductor system." Nature Methods, vol. 10, No. 7, Jul. 2013.

U.S. Appl. No. 13/480,161, filed May 24, 2012.

Mandavifar, et al. "Implementation of a Polysilicon Micro Electro-Thermal Detector in Gas Chromatography System with Applications in Portable Environmental Monitoring." ECS Journal of Solid State Science and Technology, 4 (10) S3062-S3066 (2015). Aug. 28, 2015.

Scorzoni, et al. "Thermal Characterization of a Thin Film Heater on Glass Substrate for Lab-on-Chip Applications." 2014 IEEE International Instrumentation and Measurement Technology Conference (I2MTC) Proceedings. May 12, 2014.

U.S. Appl. No. 14/719,991, filed May 22, 2015.

Non-Final Office Action dated Feb. 2, 2016 for U.S. Appl. No. 14/719,991.

U.S. Appl. No. 14/713,543, filed May 15, 2015.

Non-Final Office Action dated Jul. 18, 2016 for U.S. Appl. No. 14/713,543.

Final Office Action dated Aug. 12, 2016 U.S. Appl. No. 14/719,991.

Non Final Office Action dated Sep. 6, 2016 U.S. Appl. No. 14/600,315.

Petrucci, et al. "Thermal Characterization of Thin Film Heater for Lab-on-Chip Application." 2015 XVIII AISEM Annual Conference. Feb. 2015.

Nanohelix.net RealHelix qPCR Kit. Published in 2009. Retrieved online at http://www.nanohelix.net/02_products/view.asp?pack_code=277.

Non-Final Office Action dated Jan. 3, 2018 in connection with U.S. Appl. No. 15/216,853.

Notice of Allowance dated Jan. 10, 2018 in connection with U.S. Appl. No. 14/719,991.

* cited by examiner

ON-CHIP REFERENCE ELECTRODE FOR BIOLOGICALLY SENSITIVE FIELD EFFECT TRANSISTOR

REFERENCE TO RELATED APPLICATION

This Application claims priority to U.S. Provisional Application No. 62/434,623 filed on Dec. 15, 2016

BACKGROUND

Biosensors are devices for sensing and detecting biological entities, and typically operate on the basis of electronic, chemical, optical, or mechanical detection principles. Detection can be performed by detecting the biological entities themselves, or through interaction and reaction between specified reactants and the biological entities. Biosensors are widely used in different life-science applications, ranging from environmental monitoring and basic life science research to Point-of-Care (PoC) in-vitro molecular diagnostics.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

The present disclosure provides many different embodiments, or examples, for implementing different features of this disclosure. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

One type of biosensor comprises a device substrate that accommodates a biologically sensitive field-effect transistor (BioFET). The BioFET comprises a source region and a drain region that are arranged within the device substrate and that define a channel region therebetween. Further, the BioFET comprises a back gate electrode arranged under the device substrate, laterally between the source region and the drain region. A sensing well is located laterally between the source region and the drain region, and lined by a bio-sensing film overlying the channel region. The bio-sensing film is configured to react with or bind to biological entities to facilitate a change in the conductance of the channel region, such that the presence of the biological entities may be detected based on the conductance of the channel region.

During operation, the biological entities are suspended within a fluid and applied to the sensing well to detect the presence of the biological entities. Further, after application of the fluid to the sensing well, the fluid may be biased to a reference potential to enhance the detection of the biological entities. An external reference electrode was employed (immersed into the fluid from top of a fluid channel) to provide the fluid a reference potential through an external power source. However, the external reference electrode is not integrated with the micro-fabricated biosensor, and may not suitable for some applications such as portable devices. Also, the external reference electrode may introduce damages and contaminations to the bio-sensing film when applied, and/or also complicate the detection procedure. Further, the external reference electrode hardly provides precise reference potential control because of its inconsistency and instability during the operations.

The present application is directed towards a semiconductor device including a biosensor with an on-chip reference electrode embedded within the semiconductor device, and associated manufacturing methods, to improve integration of the semiconductor device and provide convenient and precise reference potential control. In some embodiments, the semiconductor device comprises a device substrate. A pair of source/drain regions is disposed within the device substrate and separated by a channel region. An isolation layer is disposed over the device substrate. A sensing well is disposed from an upper surface of the isolation layer overlying the channel region. A bio-sensing film is disposed along the upper surface of the isolation layer and extended along sidewall and lower surfaces of the sensing well. A reference electrode is disposed vertically between the bio-sensing film and the isolation layer. By forming the reference electrode between the bio-sensing film and the isolation layer, the isolation can act as a barrier to prevent the reference electrode material diffusing to the device substrate. Damages and contaminations to the bio-sensing film can be reduced or even eliminated since the reference electrode is integrated within the device before forming the bio-sensing film. Also, procedures to provide reference potentials for varies biological detections are simplified compared to cleaning and immersing an external reference electrode into the fluid. Further, a more precise reference potential control can be realized.

Figure 1:
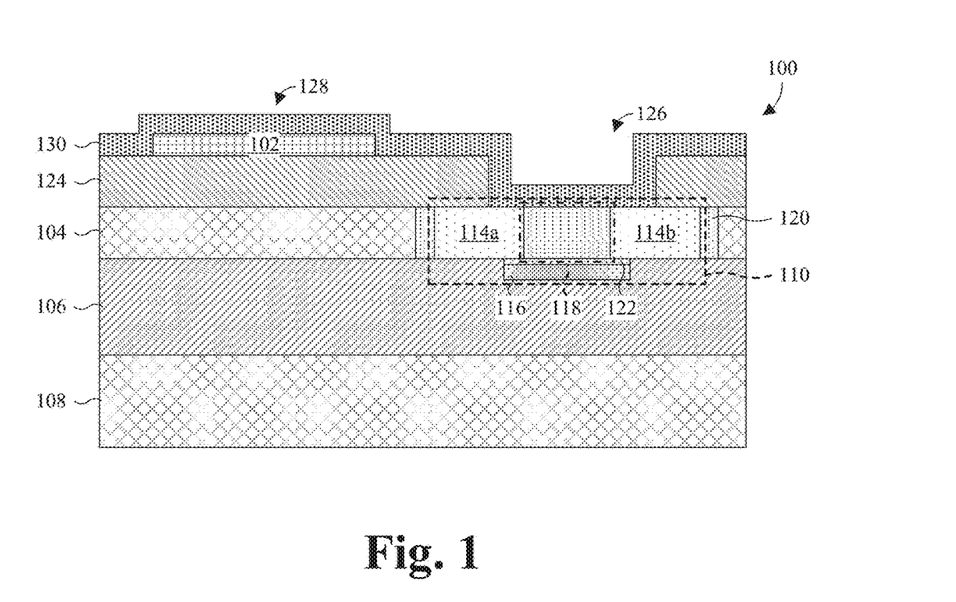
FIG. 1 illustrates a cross-sectional view of some embodiments of a semiconductor device with a biologically sensitive field effect transistor (BioFET) and an on-chip reference electrode.

With reference to FIG. 1, a cross-sectional view of a semiconductor device 100 with a reference electrode 102 is provided according to some embodiments. As illustrated, in some embodiments, a back-end-of-line (BEOL) interconnect structure 106 is arranged over a handling substrate 108 and a device substrate 104 is arranged over the BEOL interconnect structure 106. The reference electrode 102 is arranged over the device substrate 104. The handling substrate 108 may be, for example, a bulk semiconductor substrate, such as a bulk substrate of monocrystalline silicon. The device substrate 104 accommodates a BioFET 110 and may be, for example, a semiconductor layer of a semiconductor-on-insulator (SOI) substrate or a bulk semiconductor substrate.

The BioFET 110 comprises a pair of source/drain regions 114a, 114b and, in some embodiments, a back gate electrode 116. The source/drains regions 114a, 114b have a first doping type and are arranged within the device substrate 104, respectively on opposite sides of a channel region 118 of the BioFET 110. The channel region 118 has a second doping type opposite the first doping and is arranged in the device substrate 104, laterally between the source/drain regions 114a, 114b. The first and second doping types may, for example, respectively be n-type and p-type, or vice versa. In some embodiments, the BioFET 110 is arranged through the device substrate 104 extending from a top surface of the device substrate 104 to a bottom surface of the device substrate 104 as shown. In some other embodiments, the source/drain regions 114a, 114b and the channel region 118 are arranged at an underside of the device substrate 104 (lower portion of the device substrate 104). In some embodiments, the BioFET 110 is arranged within a well region 120 of the device substrate 104 that has the second doping type, and/or are electrically coupled to the BEOL interconnect structure 106. The back gate electrode 116 is arranged under the device substrate 104, laterally between the source/drain regions 114a, 114b, and is spaced from the device substrate 104 by a gate dielectric layer 122 of the BioFET 110. In some embodiments, the back gate electrode 116 is electrically coupled to the BEOL interconnect structure 106 and/or is metal, doped polysilicon, or a combination thereof.

An isolation layer 124 is arranged over the device substrate 104, and comprises a sensing well 126. The sensing well 126 extends into the isolation layer 124 to proximate the channel region 118 and is at least partially lined by a bio-sensing film 130. Further, in some embodiments, the sensing well 126 extends through the isolation layer 124 to expose the channel region 118 and/or is arranged laterally between the source/drain regions 114a, 114b. In some embodiments, the sensing well 126 and the lined bio-sensing film 130 laterally extend to cross boundaries of the channel region 118 and the source/drain regions 114a, 114b to partially cover the source/drain regions 114a, 114b. The isolation layer 124 may be, for example, silicon dioxide, a buried oxide (BOX) layer of a SOI substrate, some other dielectric, or a combination thereof. The bio-sensing film 130 lines the sensing well 126 and, in some embodiments, covers the isolation layer 124. Though not show in FIG. 1, in some other embodiments, the bio-sensing film 130 has some openings depending on applications, for example, for external wiring pads (examples also shown and discussed later in FIG. 2 and FIG. 3). Further, the bio-sensing film 130 is configured to react with or bind to biological entities to facilitate a change in the conductance of the channel region 118, such that the presence of the biological entities may be detected based on the conductance of the channel region 118. The bio-sensing film 130 may be, for example, titanium nitride, titanium, a high κ dielectric, some other material configured to react with or bind to the biological entities, or a combination thereof. The biological entities may be, for example, DNA, ribonucleic acid (RNA), drug molecules, enzymes, proteins, antibodies, antigens, or a combination thereof. The bio-sensing film 130 may include a material for any specified bio-molecule binding. In an embodiment, the bio-sensing film 130 includes a high-k dielectric material such as, $HfO_2$. In an embodiment, the bio-sensing film 130 includes a metal layer such as Pt, Au, Al, W, Cu, and/or other suitable metal. Other exemplary bio-sensing film 130 includes high-k dielectric films, metals, metal oxides, dielectrics, and/or other suitable materials. As a further example, bio-sensing film 130 includes $HfO_2$, $Ta_2O_5$, Pt, Au, W, Ti, Al, Cu, oxides of such metals, $SiO_2$, $Si_3N_4$, $Al_2O_3$, $TiO_2$, TiN, SnO, $SnO_2$; and/or other suitable materials. The bio-sensing film 130 may include a plurality of layers of material. The bio-sensing film 130 may, for example, have a thickness of less than about 100 nanometers.

In some embodiments, the reference electrode 102 is disposed indirectly or directly on the isolation layer 124 laterally next to the sensing well 126. The reference electrode 102 may be disposed indirectly or directly under the bio-sensing film 130. In some embodiments, the reference electrode 102 comprises platinum (Pt), gold (Au), silver (Ag), silver chlorine (AgCl) or the combination thereof. The reference electrode 102 may have a thickness in a range of from about 500 Å to about 1 μm. By separating the reference electrode 102 from the device substrate 104 (e.g. by the isolation layer 124), contamination introduced by the reference electrode 102 is effectively prevented. By arranging the reference electrode 102 under the bio-sensing film 130, no additional passivation layer is needed for the reference electrode 102.

While the embodiments of FIG. 1 are illustrated with the back gate electrode 116 and the gate dielectric layer 122 presented, it is appreciated that the back gate electrode 116 and the gate dielectric layer 122 may be omitted in other embodiments. Also, while the embodiments of FIG. 1 are described with the BioFET 110, the BioFET 110 may be replaced with some other type of transistor in other embodiments.

Figure 2:
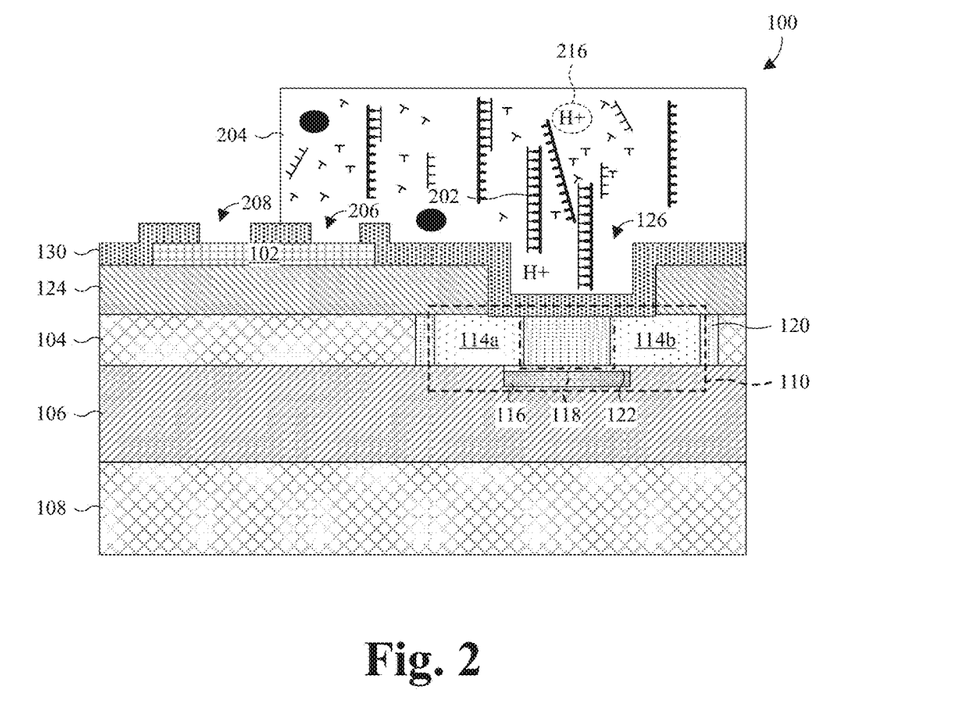
FIG. 2 illustrates a cross-sectional view of some detailed embodiments of the BioFET and the on-chip reference electrode of FIG. 1 with an in-channel reference electrode opening and an out-channel reference electrode opening.

With reference to FIG. 2, a cross-sectional view of the BioFET 110 and the reference electrode 102 of FIG. 1 with an in-channel reference electrode opening 206 and an out-channel reference electrode opening 208 is provided according to some detailed embodiments. For illustration purpose only, a process for using the semiconductor device 100 to detect a DNA segment 202 is shown in FIG. 2. The sensing well 126 is exposed to a fluid 204. The fluid 204 is an aqueous solution within which the DNA segment 202 may or may not be suspended. Other auxiliary components may also be suspended within the fluid 204, such as primers, a polymerase, or deoxynucleoside triphosphates (dNTPs). With the fluid 204 applied to the semiconductor device 100, a reference bias is applied to the reference electrode 102 through the out-channel reference electrode opening 208. In some embodiments, the reference electrode 102 is exposed to the fluid 204 through in-channel reference electrode opening 206. To the extent that the DNA segment 202 is present in the fluid 204, a thermal cycling may be performed to replicate the DNA segment 202 and increases the amount of DNA segments to a more readily detectable level. The conductance of the channel region 118 of the BioFET 110 is measured to identify the presence of DNA segments and, in some embodiments, the amount of DNA segments since the conductance of the channel region 118 varies based on the amount of DNA segments in the fluid 204. When a DNA segment lands on the bio-sensing film 130, the DNA segment binds to the bio-sensing film 130 and releases a hydrogen ion 216 into the fluid 204. The hydrogen ion 216, in turn, increases the pH of the fluid 204 and varies the conductance of the channel region 118. Therefore, as the amount of DNA segments increases, the pH of the fluid 204 increases and the extent of the change in the conductance of the channel region 118 increases.

While the embodiments of FIG. 2 are illustrated with the DNA segments being detected through pH variations of the fluid 204, it is appreciated different biological entities and different bio-detection mechanisms are amenable and can be used for varies applications.

Figure 3:
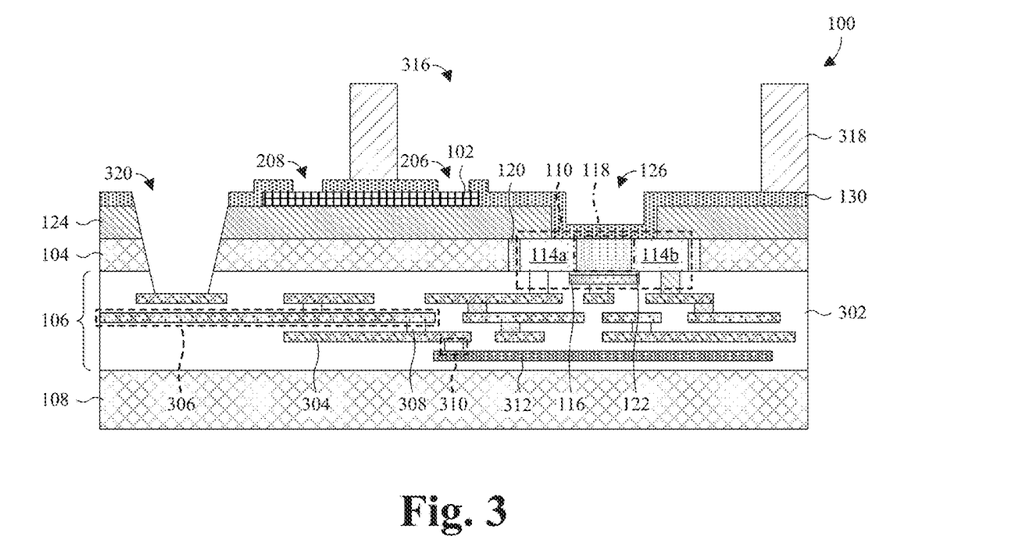
FIG. 3 illustrates a cross-sectional view of some more detailed embodiments of the BioFET and the on-chip reference electrode of FIG. 1 with a pad opening.

With reference to FIG. 3, a cross-sectional view of some more detailed embodiments of the semiconductor device 100 of FIG. 1 is provided. As illustrated, the BEOL interconnect structure 106 is arranged under the device substrate 104, between the device substrate 104 and the handling substrate 108. The BEOL interconnect structure 106 comprises an interlayer dielectric (ILD) layer 302 within which first interconnect metal layers 304 of line or pad features 306 and second interconnect metal layers 308 of via features 310 are alternatingly stacked. In some embodiments, a heater 312 is part of the BEOL interconnect structure 106 and/or is arranged over the handling substrate 108. The ILD layer 302 may be, for example, silicon dioxide, silicon nitride, a low κ dielectric, some other dielectric, or a multi-layer film comprising a combination thereof. As used herein, a low-κ dielectric is a dielectric with a dielectric constant κ less than about 3.9. The BioFET 110 arranged in the device substrate 104 is electrically coupled to some of the first and second interconnect metal layers 304, 308. Further, the reference electrode 102 may also be coupled to other of the first and second interconnect metal layers 304, 308. The first and second interconnect metal layers 304, 308 may be, for example, copper, aluminum copper, aluminum, tungsten, some other conductive material, or a combination thereof.

The isolation layer 124 is arranged over the device substrate 104. The sensing well 126 is arranged in the isolation layer and over the BioFET 110. The sensing well 126 is lined by the bio-sensing film 130 and covered by a fluidic channel 316. The fluidic channel 316 may, for example, be defined laterally between a channel structure 318 arranged over the isolation layer 124. The isolation layer 124 also accommodates a pad opening 320 apart from the fluidic channel 316. The pad opening 320 extends into the ILD layer 302, through the isolation layer 124 and the device substrate 104, to expose one of the line or pad features 306 of the first interconnect metal layers 304. Further, in some embodiments, the pad opening 320 extends through the bio-sensing film 130. Though not shown in FIG. 3, in some embodiments, wires are respectively coupled to the pad opening 320 and the out-channel reference electrode opening 208. In some other embodiments, one wire can be used to connect the out-channel reference electrode opening 208 to the pad opening 320 to provide the reference bias.

Figure 4:
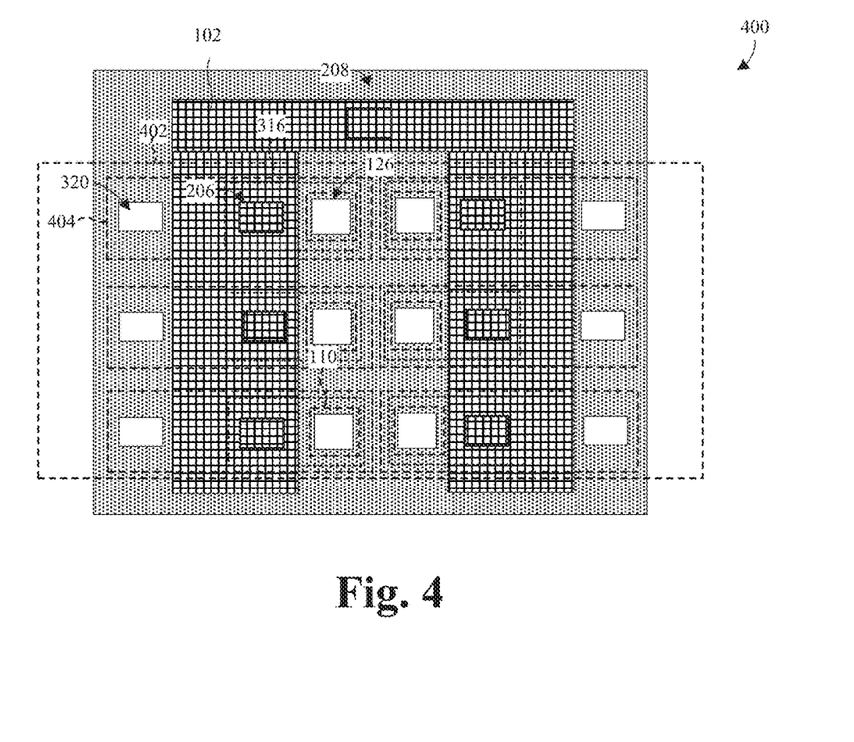
FIG. 4 illustrates a layout view of some embodiments of a semiconductor device having an array of BioFETs.

With reference to FIG. 4, a layout view 400 of a semiconductor device having an array 402 of unit cells 404 is provided according to some embodiments. As illustrated, in some embodiments, the unit cells 404 are arranged in rows and columns. Each of the unit cells 404 can comprise a sensing well 126 overlying a BioFET 110. The sensing well 126 may cover a channel region of the bioFET 110. A reference electrode 102 is arranged aside from the sensing well 126. The reference electrode 102 is at least partially exposed to a fluid channel 316, through an in-channel reference electrode opening 206 for example. In some embodiments, an out-channel reference electrode opening 208 is used to provide a contact point for reference bias source. The out-channel reference electrode opening 208 may be shared by more than one unit cells 404. A pad opening 320 can be arranged laterally next to the reference electrode, to expose one or more of the metal line or pad features 306 in metal interconnect structure 106. Examples of structure of the unit cells 404 are shown in FIG. 1, FIG. 2, or FIG. 3.

With reference to FIGS. 5-14, a series of cross-sectional views 500-1400 of some embodiments of a method for manufacturing a semiconductor device with a BioFET and an on-chip reference electrode is provided.

Figure 5:
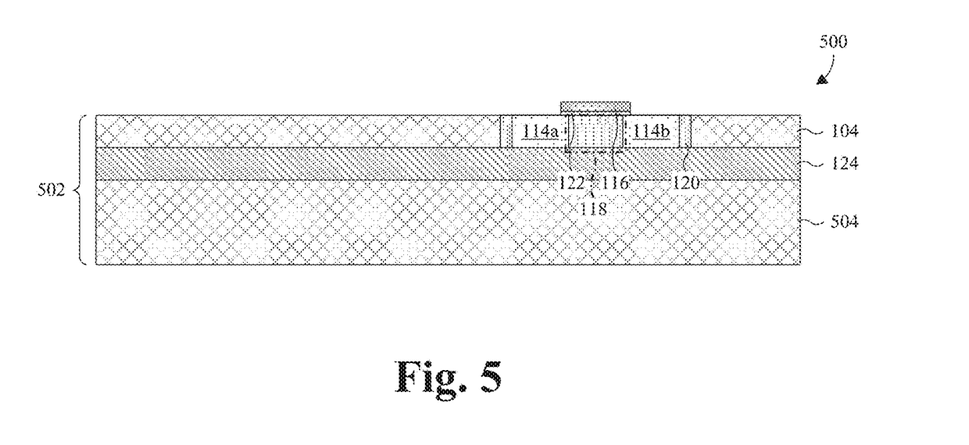
FIGS. 5-14 illustrate a series of cross-sectional views of some embodiments of a method for manufacturing a semiconductor device with a BioFET and an on-chip reference electrode.

As illustrated by the cross-sectional view 500 of FIG. 5, an SOI substrate 502 is provided. The SOI substrate 502 comprises a bulk semiconductor substrate 504 over which an isolation layer 124 and a device substrate 104 are stacked. As seen hereafter, the bulk semiconductor substrate 504 is a sacrificial substrate (will be removed later). The bulk semiconductor substrate 504 and the device substrate 104 may be, for example, monocrystalline silicon, and/or the isolation layer 124 may be, for example, silicon dioxide.

A pair of source/drain regions 114a, 114b is formed in the device substrate 104, such that the source/drain regions 114a, 114b are laterally spaced from one another. For example, ions may be implanted into the device substrate 104 to form the source/drain regions 114a, 114b in the device substrate 104. The source/drain regions 114a, 114b are formed with a first doping type and are formed in a region of the device substrate 104 that has a second doping type opposite the first doping type, such that a channel region 118 is formed in the device substrate 104 between the source/drain regions 114a, 114b. In some embodiments, the region within which the source/drain regions 114a, 114b are formed is a bulk of the device substrate 104, such that the device substrate 104 has the second doping type. In other embodiments, the region within which the source/drain regions 114a, 114b are formed is a well region 120 of the device substrate 104. The well region 120 may be formed before the source/drain regions 114a, 114b by, for example, ion implantation.

In some embodiments, a back gate electrode 116 and a gate dielectric layer 122 are formed stacked over the channel region 118, laterally between the source/drain regions 114a, 114b. In some embodiments, the process for forming the back gate electrode 116 and the gate dielectric layer 122 comprises sequentially depositing or growing a dielectric layer and a conductive layer stacked over the device substrate 104. For example, the dielectric and conductive layers may be deposited or grown by, for example, thermal oxidation, electro chemical plating (ECP), vapor deposition, sputtering, or a combination thereof. Further, in some embodiments, the process comprises patterning the dielectric and conductive layers using, for example, photolithography to selectively etch the dielectric and conductive layers respectively into the gate dielectric layer 122 and the back gate electrode 116.

Figure 6:
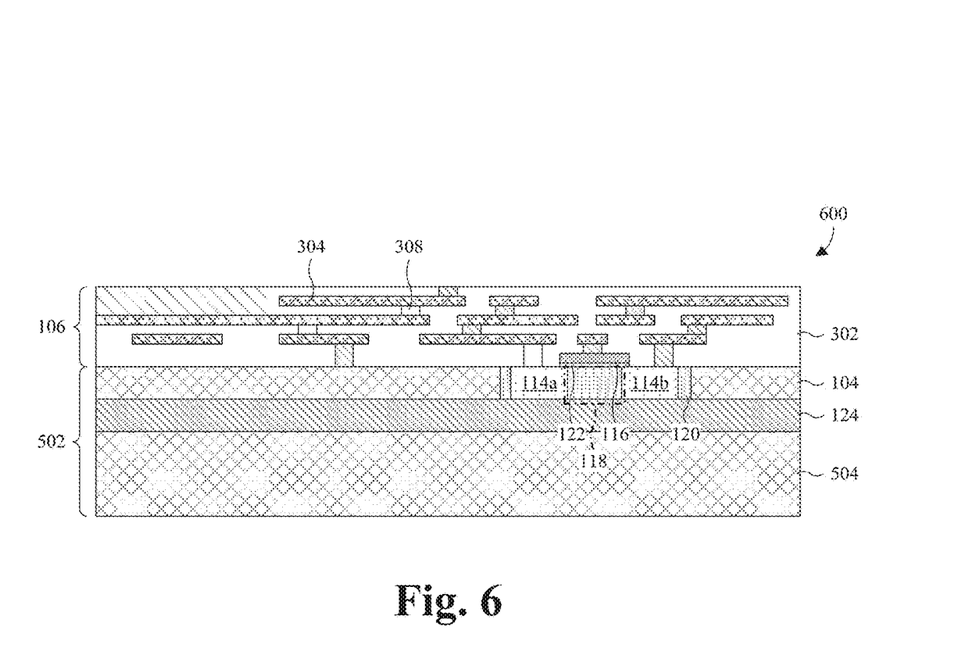

As illustrated by the cross-sectional view 600 of FIG. 6, a BEOL interconnect structure 106 is partially formed over the SOI substrate 502. The BEOL interconnect structure 106 is formed with first interconnect metal layers 304 of line or pad features and second interconnect metal layers 308 of via features alternatingly stacked within an ILD layer 302. The first and second interconnect metal layers 304, 308 may be, for example, formed by a single-damascene-like process or a dual-damascene-like process. A single-damascene-like or dual-damascene-like process is a single-damascene or dual-damascene process that is not restricted to copper. Though not shown in FIG. 6 and the subsequent figures, in some embodiments, a heater (e.g. the heater 312 shown in FIG. 3) can be formed within the ILD layer 302 or formed within an additional ILD layer over the BEOL interconnect structure 106.

Figure 7:
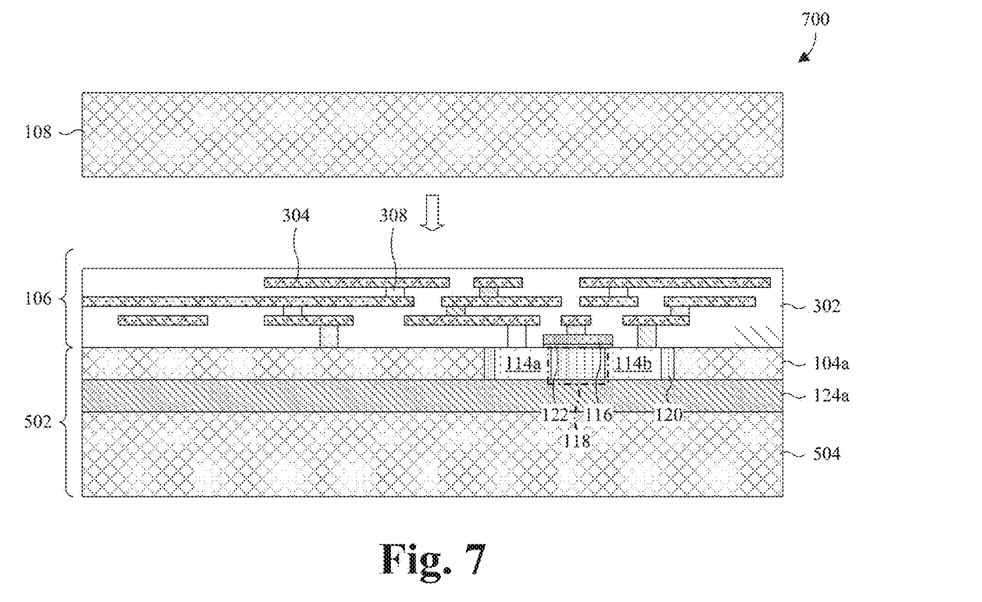

As illustrated by the cross-sectional view 700 of FIG. 7, a handling substrate 108 is bonded to the SOI substrate 502 through the BEOL interconnect structure 106. For example, the handling substrate 108 may be bonded to the BEOL interconnect structure 106 by a fusion bonding process, such as a hydrophilic fusion bonding process. The fusion bonding process is applicable for $SiO_2$ to Si bonding, Si to Si bonding, and other suitable bonding. In one or more embodiments, $SiO_2$ to Si fusion bonding occurs between the ILD layer 302 (e.g., $SiO_2$) and the handling substrate 108 (e.g., Si).

Figure 8:
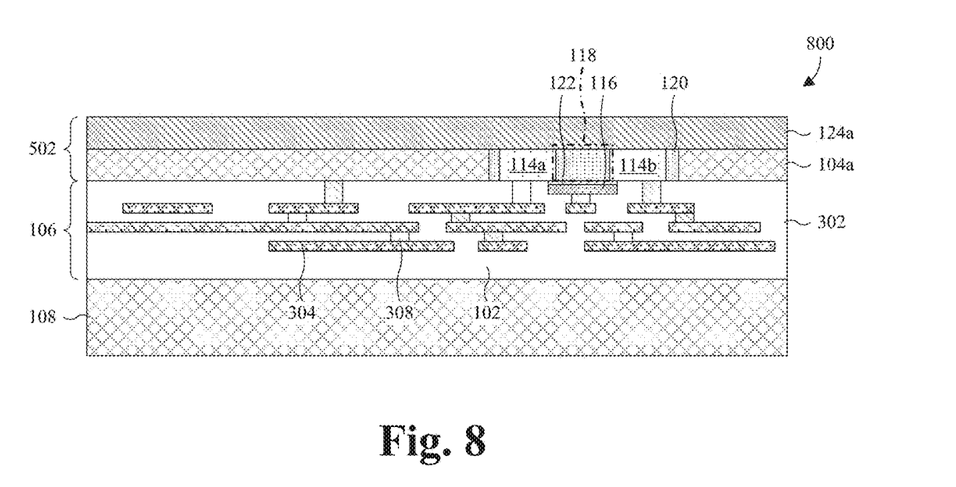

As illustrated by the cross-sectional view 800 of FIG. 8, the structure of FIG. 7 is flipped vertically and the SOI substrate 502 is thinned to partially or completely remove the bulk semiconductor substrate 504 (see, e.g., FIG. 7). In some embodiments, the bulk semiconductor substrate 504 is removed by grinding, CMP, etching back, or a combination thereof.

Figure 9:
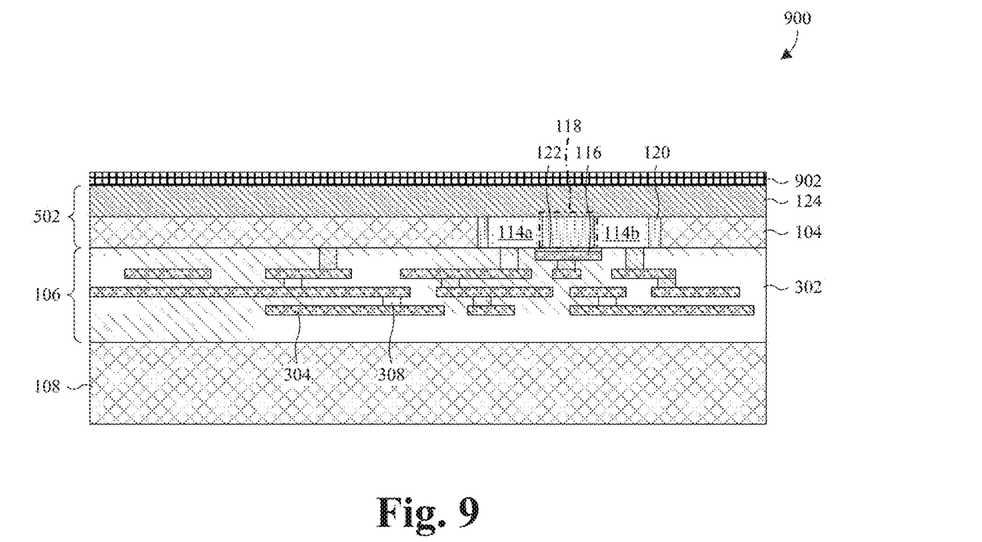

As illustrated by the cross-sectional view 900 of FIG. 9, a reference electrode layer 902 is formed on the isolation layer 124 over the device substrate 104 at an opposite side of the device substrate 104 as BEOL interconnect structure 106. In some embodiments, the reference electrode layer 902 can be formed using metal materials such as platinum (Pt), gold (Au), silver (Ag), silver chlorine (AgCl) or the combination thereof. In some embodiments, the reference electrode layer 902 can be formed using physical or chemical deposition processes including but not limited to electron beam deposition or sputtering deposition processes. The reference electrode layer 902 can also be formed using electroplating or screen printing processes (for silver material for example).

Figure 10:
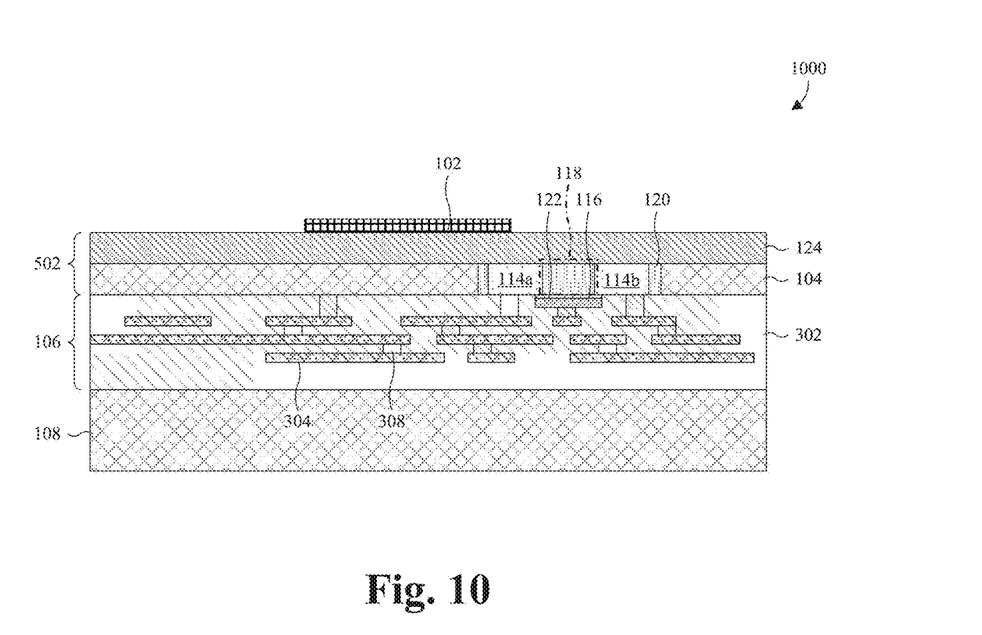

As illustrated by the cross-sectional views 1000 of FIG. 10, the reference electrode layer 902 (shown in FIG. 9) is patterned to form the reference electrode 102. In some embodiments, the reference electrode layer 902 (shown in FIG. 9) is patterned by dry and/or wet etching processes, including but not limited to a lift-off process, an ion beam etching (IBE) process, a reactive-ion etching (RIE) process, and/or a wet etching process using aqua regia, potassium iodide, or iodine solution.

Figure 11:
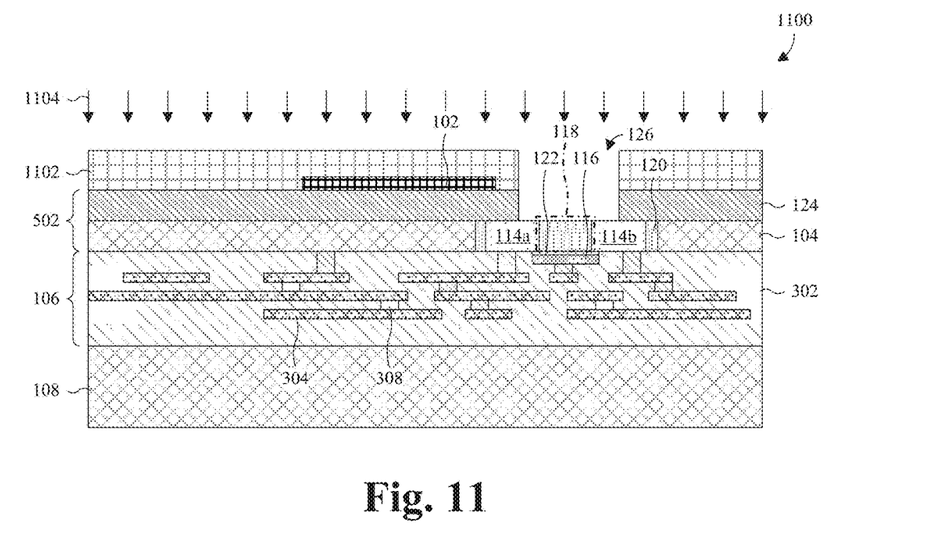

As illustrated by the cross-sectional view 1100 of FIG. 11, a first etch is performed into an isolation layer 124 to form a sensing well 126 laterally between the source/drain regions 114a, 114b and, in some embodiments, exposing the channel region 118. The process for performing the first etch may comprise, for example, depositing or growing a first photoresist layer 1102 over the isolation layer 124. Further, the process may comprise, for example, patterning the first photoresist layer 1102 using photolithography, such that the first photoresist layer 1102 comprises one or more openings corresponding to the sensing well 126 and/or the heating well 128. With the first photoresist layer 1102 patterned, the process may comprise, for example, applying one or more first etchants 1104 to the isolation layer 124 with the first photoresist layer 1002 in place, and subsequently stripping the first photoresist layer 1102.

Figure 12:
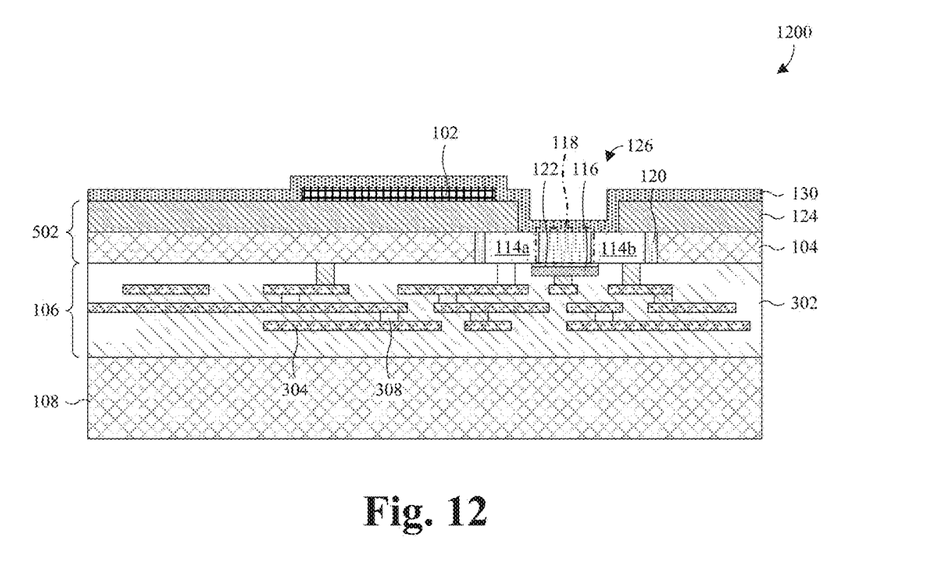

As illustrated by the cross-sectional view 1200 of FIG. 12, a bio-sensing film 130 is formed lining the sensing well 126. In some embodiments, the bio-sensing film 130 is formed conformally, and/or is formed of a high κ dielectric, or a combination thereof. The process for forming the bio-sensing film 130 may comprise depositing or growing the bio-sensing film 130 covering the isolation layer 124 and lining the sensing well 126. The bio-sensing film 130 may be deposited or grown by, for example, vapor deposition, sputtering, atomic layer deposition (ALD), or a combination thereof.

Figure 13:
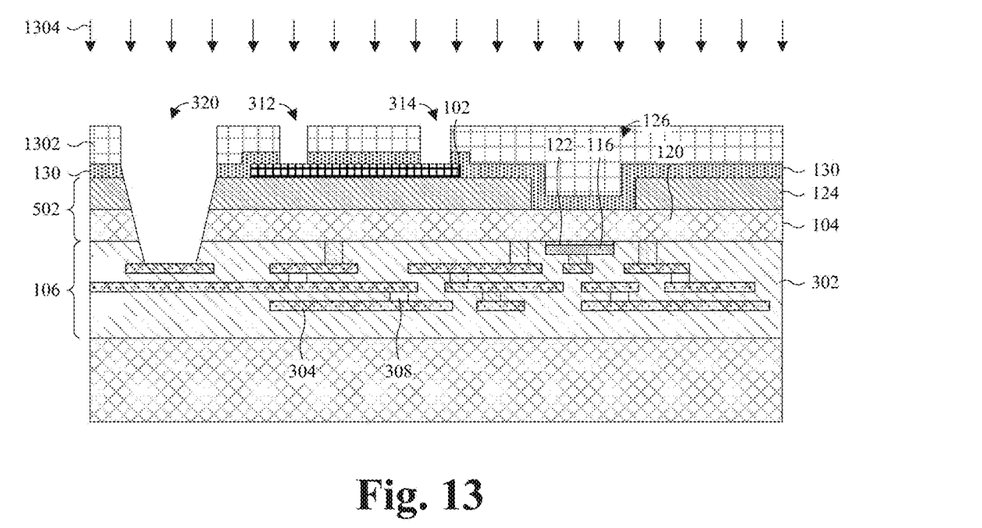

As illustrated by the cross-sectional view 1300 of FIG. 13, in some embodiments, a second etch is performed into the isolation layer 124, the device substrate 104, and the ILD layer 302 to form a pad opening 320 exposing one of the first interconnect metal layers 304 of the BEOL interconnect structure 106. Further, in some embodiments, the second etch is performed through the bio-sensing film 130, and/or is formed along the periphery of the device substrate 104 and the BEOL interconnect structure 106. The process for performing the second etch may comprise, for example, depositing or growing a second photoresist layer 1302 over the isolation layer 124 and/or the bio-sensing film 130. Further, the process may comprise, for example, patterning the second photoresist layer 1302 using photolithography, such that the second photoresist layer 1302 comprises an opening corresponding to the pad opening 320. With the second photoresist layer 1302 patterned, the process may comprise, for example, applying one or more second etchants 1304 to the isolation layer 124, the device substrate 104, and the ILD layer 302 with the second photoresist layer 1302 in place, and subsequently stripping the second photoresist layer 1302.

Figure 14:
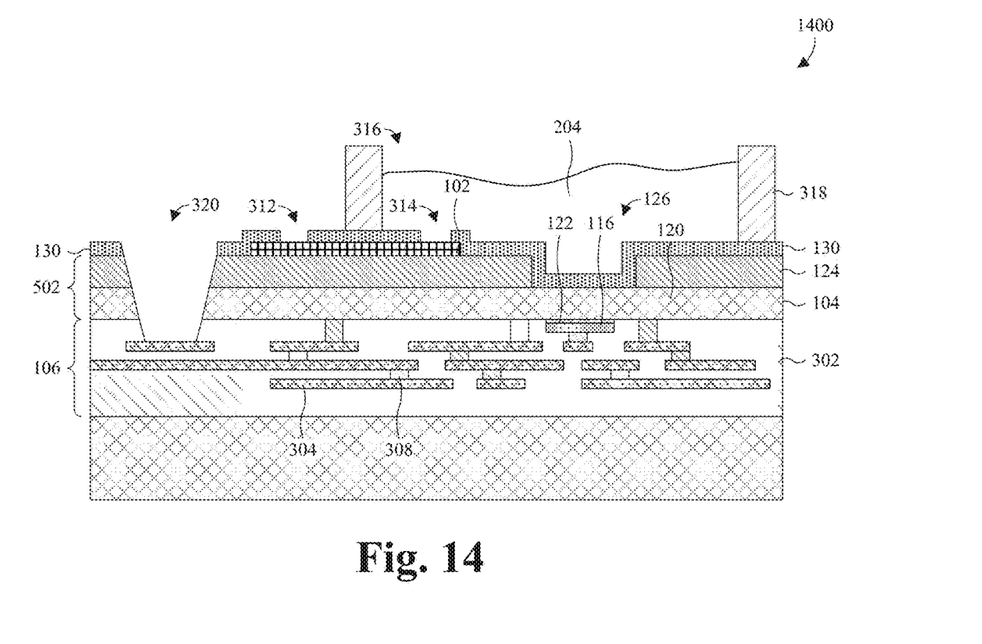

As illustrated by the cross-sectional view 1400 of FIG. 14, a channel structure 318 is formed over the isolation layer 124 and, in some embodiments, the bio-sensing film 130 to define a fluidic channel 316 over the sensing well 126. The channel structure 318 may, for example, be formed, such that the fluidic channel 316 is covered or exposed to a surrounding environment of the semiconductor device. Further, the channel structure 318 may, for example, be formed with a microelectromechanical systems (MEMS) device to control the flow and/or circulation of fluid through the fluidic channel 316. The channel structure 318 can be made of plastic, polymer or other applicable materials. Notably, the channel structure 318 may not be an essential component of the semiconductor device and may also be a separate component that is capable to be assembled to the semiconductor device to enhance the detection.

Figure 15:
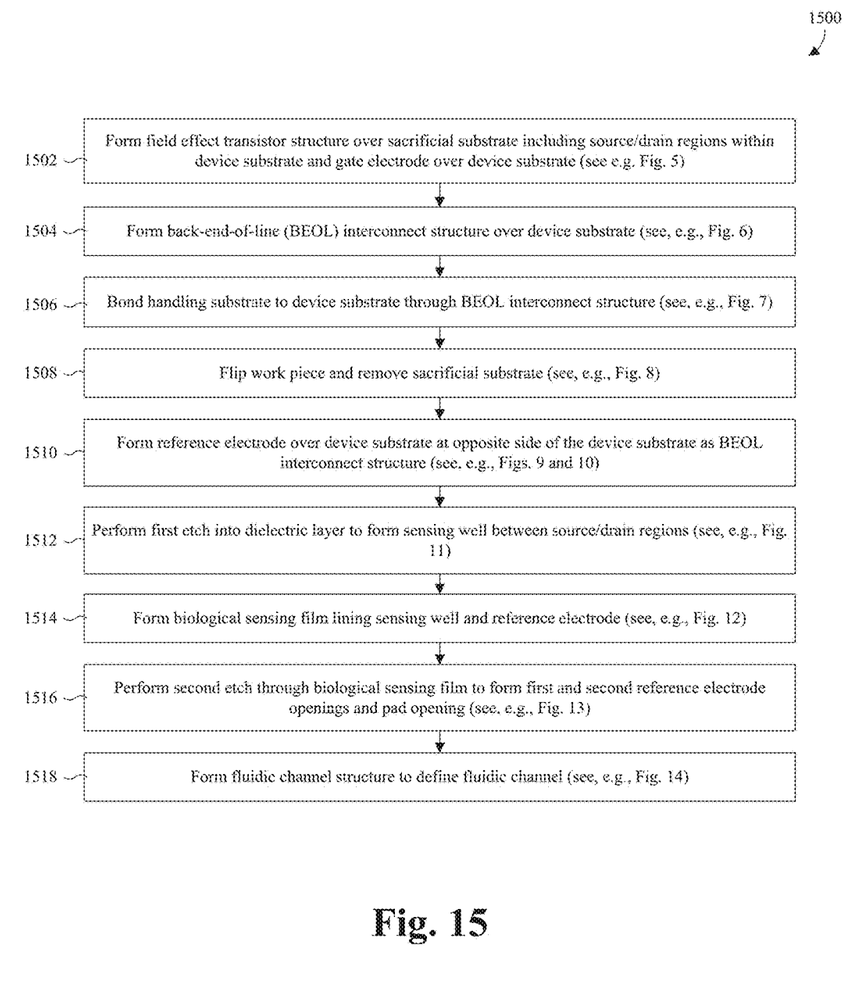
FIG. 15 illustrates a flowchart of some embodiments of the method of FIGS. 5-14.

With reference to FIG. 15, a flowchart 1500 of some embodiments of the method of FIGS. 5-14 is provided.

At 1502, source/drain regions are formed with a device substrate. In some embodiments, the device substrate is a semiconductor layer of a SOI substrate arranged over a dielectric layer and a bulk semiconductor substrate. The bulk semiconductor substrate may be a sacrificial substrate that is removed in a later manufacturing stage. The dielectric layer may act as an isolation layer for the work piece. FIG. 5 illustrates some embodiments of a cross-sectional view 500 corresponding to act 1502.

At 1504, a BEOL interconnect structure is formed over the device substrate. FIG. 6 illustrates some embodiments of a cross-sectional view 600 corresponding to act 1504.

At 1506, a handling substrate is bonded to the semiconductor substrate through the BEOL interconnect structure.

For example, the handling substrate may be bonded to the BEOL interconnect structure by a fusion bonding process. FIG. 7 illustrates some embodiments of a cross-sectional view 700 corresponding to act 1506.

At 1508, the work piece is flipped and the sacrificial substrate is partially or completely removed. In some embodiments, the sacrificial substrate is removed by grinding, CMP, etching back, or a combination thereof. FIG. 8 illustrates some embodiments of a cross-sectional view 800 corresponding to act 1508.

At 1510, a reference electrode layer is formed over the isolation layer and patterned to form a reference electrode. The isolation layer prevents the reference electrode from diffusing into the device substrate. FIGS. 9-10 illustrate some embodiments of cross-sectional views 900-1000 corresponding to act 1510.

At 1512, a first etch is performed into the isolation layer to form a sensing well between the source/drain regions. FIG. 11 illustrates some embodiments of a cross-sectional view 1100 corresponding to act 1512.

At 1514, a bio-sensing film is formed lining the sensing well. In some embodiments, the bio-sensing film is formed of titanium nitride, titanium, a high κ dielectric, or a combination thereof. The bio-sensing film may also line the reference electrode layer and act as a barrier layer or a passivation layer. FIG. 12 illustrates some embodiments of a cross-sectional view 1200 corresponding to act 1514.

At 1516, a second etch is performed into the BEOL interconnect structure, through the isolation layer and the device substrate, and an upper portion of the BEOL interconnect structure to form a pad opening. In some embodiments, the second etch is also performed through the bio-sensing film. FIG. 13 illustrates some embodiments of a cross-sectional view 1300 corresponding to act 1516.

At 1518, a channel structure is formed on the isolation layer to define a fluidic channel. FIG. 14 illustrates some embodiments of a cross-sectional view 1400 corresponding to act 1518.

While the method described by the flowchart 1500 is illustrated and described herein as a series of acts or events, it will be appreciated that the illustrated ordering of such acts or events are not to be interpreted in a limiting sense. For example, some acts may occur in different orders and/or concurrently with other acts or events apart from those illustrated and/or described herein. Further, not all illustrated acts may be required to implement one or more aspects or embodiments of the description herein, and one or more of the acts depicted herein may be carried out in one or more separate acts and/or phases.

Therefore, the present disclosure relates to a semiconductor device including a biosensor with an on-chip reference electrode embedded within the semiconductor device, and associated manufacturing methods. By integrating the reference electrode into the semiconductor device, convenient and precise reference potential control is provided.

In some embodiments, the present disclosure provides a semiconductor device. A pair of source/drain regions is disposed within a device substrate and separated by a channel region. An isolation layer is disposed over the device substrate. A sensing well is disposed from an upper surface of the isolation layer overlying the channel region. A bio-sensing film is disposed along the upper surface of the isolation layer and extended along sidewall and lower surfaces of the sensing well. A reference electrode is disposed vertically between the bio-sensing film and the isolation layer.

In other embodiments, the present disclosure provides another semiconductor device. An interconnect structure is disposed over a handling substrate, and comprises a plurality of metal layers disposed within a dielectric layer. A device substrate is disposed over the interconnect structure, and comprises a biologically sensitive field effect transistor (BioFET) disposed therein including a pair of source/drain regions and separated by a channel region. An isolation layer is disposed over the device substrate, and a sensing well is disposed from an upper surface of the isolation layer overlying the channel. A reference electrode disposed on the isolation layer aside of the sensing well.

In yet other embodiments, the present disclosure provides a method for manufacturing a semiconductor device. The method comprises providing a semiconductor-on-insulator (SOI) substrate comprising an isolation layer disposed over a sacrificial substrate and a device substrate disposed over the isolation layer, and forming a biological field effect transistor within the device substrate comprising a channel region between a pair of source/drain regions. The method further comprises bonding a handing wafer to the device substrate, and removing the sacrificial substrate. The method further comprises forming and patterning a reference electrode over the isolation layer, and forming a sensing well through the isolation layer to expose the biological field effect transistor. The method further comprises forming and patterning a bio-sensing film over the reference electrode and along upper and sidewall surfaces of the sensing well.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A semiconductor device, comprising:
   a pair of source/drain regions disposed within a device substrate and separated by a channel region;
   an isolation layer disposed over the device substrate;
   a sensing well disposed from an upper surface of the isolation layer overlying the channel region;
   a bio-sensing film disposed along the upper surface of the isolation layer and extended along sidewall and lower surfaces of the sensing well;
   a fluidic channel disposed over the bio-sensing film surrounding the sensing well; and
   a reference electrode disposed vertically between the bio-sensing film and the isolation layer;
   wherein the bio-sensing film is in direct contact with the isolation layer and the reference electrode and comprises an in-channel reference electrode opening exposing the reference electrode to the fluidic channel.

2. The semiconductor device according to claim 1, wherein the reference electrode is disposed directly on and along the upper surface of the isolation layer.

3. The semiconductor device according to claim 1, further comprising:
   a handling substrate disposed under the device substrate; and an interconnect structure disposed between the handling substrate and the device substrate, and comprising a plurality of metal layers disposed within a dielectric layer.

4. The semiconductor device according to claim 1, wherein the sensing well extends through the isolation layer to an upper surface of the channel region.

5. The semiconductor device according to claim 1, wherein the pair of source/drain regions extends from a top surface of the device substrate to a bottom surface of the device substrate.

6. The semiconductor device according to claim 1, further comprising:
a back gate electrode disposed under the channel region and separated from the channel region by a gate dielectric.

7. The semiconductor device according to claim 1, wherein the reference electrode comprises platinum, gold, silver or silver chlorine.

8. The semiconductor device according to claim 1, wherein the sensing well covers the channel region and partially covers the pair of source/drain regions.

9. The semiconductor device according to claim 1, wherein the bio-sensing film further comprises an out-channel reference electrode opening outside the fluidic channel.

10. The semiconductor device according to claim 1, wherein the reference electrode is disposed underneath the bio-sensing film and is exposed to a fluid applied to the fluidic channel during operation.

11. A semiconductor device, comprising:
an interconnect structure disposed over a handling substrate, and comprising a plurality of metal layers disposed within a dielectric layer;
a device substrate over the interconnect structure, and comprising a biologically sensitive field effect transistor (BioFET) disposed therein including a pair of source/drain regions and separated by a channel region;
an isolation layer disposed over the device substrate;
a sensing well disposed from an upper surface of the isolation layer overlying the channel region; and
a reference electrode disposed on the isolation layer aside of the sensing well;
wherein the reference electrode is disposed underneath a fluidic channel, and laterally crosses a boundary of the fluidic channel.

12. The semiconductor device according to claim 11,
wherein the reference electrode comprises platinum, gold, silver or silver chlorine; and
wherein the metal layers comprise copper.

13. The semiconductor device according to claim 11, further comprising:
a bio-sensing film disposed along an upper surface of the isolation layer, extended along sidewall and lower surfaces of the sensing well, and further extended over the reference electrode.

14. The semiconductor device according to claim 13, wherein the bio-sensing film comprises an in-channel reference electrode opening configured to expose the reference electrode to the fluidic channel to provide a reference potential to a fluid in the fluidic channel during operation.

15. The semiconductor device according to claim 11, further comprising:
a back gate electrode and a gate dielectric disposed between the pair of source/drain regions near an upper surface of the dielectric layer.

16. The semiconductor device according to claim 11, further comprising:
a pad opening extending through the isolation layer and the device substrate, and extending into the dielectric layer to expose a metal layer of the interconnect structure.

17. The semiconductor device according to claim 11, wherein the sensing well overlies the channel region and extends to neighboring portions of the source/drain regions.

18. A method for manufacturing a semiconductor device, the method comprising:
providing a semiconductor-on-insulator (SOI) substrate comprising an isolation layer disposed over a sacrificial substrate and a device substrate disposed over the isolation layer;
forming a biological field effect transistor within the device substrate comprising a channel region between a pair of source/drain regions;
bonding a handing wafer to the device substrate;
removing the sacrificial substrate;
forming and patterning a reference electrode over the isolation layer;
forming a sensing well through the isolation layer to expose the biological field effect transistor;
forming a bio-sensing film over the reference electrode and along upper and sidewall surfaces of the sensing well;
forming a channel structure over the bio-sensing film defining a fluidic channel laterally within the channel structure; and
patterning the bio-sensing film to form an in-channel reference electrode opening exposing the reference electrode to the fluidic channel.

19. The method according to claim 18, further comprising:
forming a back-end-of-line (BEOL) interconnect structure on a first side of the device substrate;
after forming the BEOL interconnect structure, thinning the SOI substrate to remove the sacrificial substrate and to expose the isolation layer; and
forming the reference electrode directly on the isolation layer.

20. The method according to claim 18, further comprising:
forming the source/drain regions extending through the device substrate from a top surface of the device substrate to a bottom surface of the device substrate.

* * * * *